(12) United States Patent
Cheng

(10) Patent No.: US 7,879,816 B2
(45) Date of Patent: Feb. 1, 2011

(54) METHODS OF TREATING CANCER AND OTHER CONDITIONS OR DISEASE STATES USING LFMAU AND LDT

(75) Inventor: Yung-chi Cheng, Woodbridge, CT (US)

(73) Assignee: Yale University, New Haven, CT (US)

( * ) Notice: Subject to any disclaimer, the term of this patent is extended or adjusted under 35 U.S.C. 154(b) by 299 days.

(21) Appl. No.: 11/921,194

(22) PCT Filed: Jun. 5, 2006

(86) PCT No.: PCT/US2006/021742
§ 371 (c)(1),
(2), (4) Date: Dec. 5, 2007

(87) PCT Pub. No.: WO2006/133092
PCT Pub. Date: Dec. 14, 2006

(65) Prior Publication Data
US 2008/0292687 A1     Nov. 27, 2008

Related U.S. Application Data

(60) Provisional application No. 60/741,728, filed on Dec. 2, 2005, provisional application No. 60/688,159, filed on Jun. 7, 2005.

(51) Int. Cl.
*A01N 43/04* (2006.01)
*A61K 31/70* (2006.01)
(52) U.S. Cl. .................. 514/50; 514/42; 514/43; 514/49; 514/51
(58) Field of Classification Search .................... None
See application file for complete search history.

(56) References Cited

U.S. PATENT DOCUMENTS

| | | |
|---|---|---|
| 4,000,137 A | 12/1976 | Dvonch et al. |
| 4,336,381 A | 6/1982 | Nagata et al. |
| 5,565,438 A | 10/1996 | Chu et al. |
| 5,567,688 A | 10/1996 | Chu et al. |
| 5,587,362 A | 12/1996 | Chu et al. |
| 5,808,040 A | 9/1998 | Chu et al. |
| 5,817,667 A | 10/1998 | Chu et al. |
| 6,063,787 A | 5/2000 | Chu et al. |
| 6,258,790 B1 | 7/2001 | Bennett et al. |
| 6,303,773 B1 | 10/2001 | Bellon et al. |
| 6,894,159 B2 | 5/2005 | Chu et al. |
| 2003/0225029 A1* | 12/2003 | Stuyver .................. 514/49 |
| 2005/0059632 A1 | 3/2005 | Storer et al. |

FOREIGN PATENT DOCUMENTS

| | | |
|---|---|---|
| JP | 50-50383 | 5/1975 |
| JP | 50-50384 | 5/1975 |
| JP | 50-64281 | 5/1975 |
| JP | 51-146482 | 12/1976 |
| JP | 53-84981 | 7/1978 |
| WO | WO9520595 | 8/1995 |
| WO | 9607413 | 3/1996 |
| WO | WO9613512 | 5/1996 |
| WO | WO9711087 | 3/1997 |

OTHER PUBLICATIONS

Cheng Cancer Letters (2001), vol. 162, pp. 533-537.*
Cheng Y-C, "Potential use of antiviral L(-)nucleoside analogues for the prevention or treatment of viral associated cancers", Cancer Letters 162 (2001) 533-537.
Krishnan, Preethi, "Novel Role of 3-Phosphoglycerate Kinase, a Glycolytic Enzyme, in the Activation of L-Nucleoside Analogs, a New Class of Anticancer and Antiviral Agents", J. Biol. Chem. 278 (2003) 36726-36732.

* cited by examiner

*Primary Examiner*—Patrick T Lewis
(74) *Attorney, Agent, or Firm*—Henry D. Coleman; R. Neil Sudol; William J. Sapone

(57) ABSTRACT

The present invention relates to the use of the compound according to formula (I), below for the treatment of tumors, cancer and hyperproliferative diseases, among other conditions or disease states: Where X is H or F; $R^1$ and $R^2$ are independently H, an acyl group, a $C_1$-$C_{20}$ alkyl or ether group, a phosphate, diphosphate, triphosphate or a phosphodiester group, a (A) or (B) group; Where Nu is a radical of a biologically active compound such as an anticancer, antiviral or antihyperproliferative compound such that an amino group or hydroxyl group from said biologically active agent forms a phosphate, phosphoramidate, carbonate or urethane group with the adjacent moiety; each $R^8$ is independently H, or a $C_1$-$C_{20}$ alkyl or ether group, preferably a $C_1$-$C_{12}$ alkyl group; k is 0-12, preferably, 0-2; and pharmaceutically acceptable salts thereof.

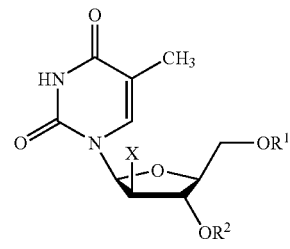

(I)

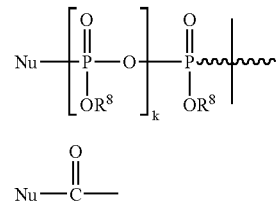

(A)

(B)

42 Claims, 12 Drawing Sheets

Effect of L-Thymidine Nucleosides on the Anticancer Activity of 5-FU/LV in C57BL6 females Bearing Colon 38

Effect of L-Thymidine Nucleoside Analogs on the Anticancer Activity of Oxaliplatin in C57BL6 Females Bearing Colon 38

Effect of L-FMAU on Gemcibine
Females Bearing Colon 38 (Exp # 17)

METHODS OF TREATING CANCER AND OTHER CONDITIONS OR DISEASE STATES USING LFMAU AND LDT

RELATED APPLICATIONS

This application claims the benefit of priority of U.S. provisional application No. 60/688,159, filed Jun. 7, 2005 and U.S. provisional application No. 60/741,728, filed Dec. 2, 2005, both of which applications are incorporated by reference in their entirety herein.

FIELD OF THE INVENTION

This invention relates to the use of 2'-fluoro-5-methyl-β-L-arabinofuranosyluridine (LFMAU or clevudine) or its related analog, β-L-2'-deoxyribofuranosylthymidine (L-deoxythymidine, LDT, L-dT or telbivudine) or conjugates comprising these agents alone or along with another active agent or prodrugs in the treatment of tumors, including cancer, and hyperproliferative diseases, chronic inflammatory diseases and certain viral and other microbial infections alone or in combination with another agent.

BACKGROUND OF THE INVENTION

A tumor is an unregulated, disorganized proliferation of cell growth. A tumor is malignant, or cancerous, if it has the properties of invasiveness and metastasis. Invasiveness refers to the tendency of a tumor to enter surrounding tissue, breaking through the basal laminas that define the boundaries of the tissues, thereby often entering the body's circulatory system. Metastasis refers to the tendency of a tumor to migrate to other areas of the body and establish areas of proliferation away from the site of initial appearance.

Cancer is now the second leading cause of death in the United States. Over 8,000,000 persons in the United States have been diagnosed with cancer, with 1,208,000 new diagnoses expected in 1994. Over 500,000 people die annually from the disease in this country.

Cancer is not fully understood on the molecular level. It is known that exposure of a cell to a carcinogen such as certain viruses, certain chemicals, or radiation, leads to DNA alteration that inactivates a "suppressive" gene or activates an "oncogene". Suppressive genes are growth regulatory genes, which upon mutation, can no longer control cell growth. Oncogenes are initially normal genes (called prooncogenes) that by mutation or altered context of expression become transforming genes. The products of transforming genes cause inappropriate cell growth. More than twenty different normal cellular genes can become oncogenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

All of the various cell types of the body can be transformed into benign or malignant tumor cells. The most frequent tumor site is lung, followed by colorectal, breast, prostate, bladder, pancreas, and then ovary. Other prevalent types of cancer include leukemia, central nervous system cancers, including brain cancer, melanoma, lymphoma, erythroleukemia, uterine cancer, and head and neck cancer.

Cancer is now primarily treated with one or a combination of three types of therapies: surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia.

Chemotherapy involves the disruption of cell replication or cell metabolism. It is used most often in the treatment of leukemia, as well as breast, lung, and testicular cancer.

There are five major classes of chemotherapeutic agents in use for the treatment of cancer: natural products and their derivatives; anthracyclines; alkylating agents; antiproliferatives (also called antimetabolites); and hormonal agents. Chemotherapeutic agents are often referred to as antineoplastic agents.

The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue.

Antimetabolites are typically reversible or irreversible enzyme inhibitors, or compounds that otherwise interfere with the replication, translation or transcription of nucleic acids.

Several synthetic nucleosides have been identified that exhibit anticancer activity. A well known nucleoside derivative with strong anticancer activity is 5-fluorouracil. 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381, and in Japanese patent publication Nos. 50-50383, 50-50384, 50-64281, 51-146482, and 53-84981.

U.S. Pat. No. 4,000,137 discloses that the peroxidate oxidation product of inosine, adenosine, or cytidine with methanol or ethanol has activity against lymphocytic leukemia.

Cytosine arabinoside (also referred to as Cytarabin, araC, and Cytosar) is a nucleoside analog of deoxycytidine that was first synthesized in 1950 and introduced into clinical medicine in 1963. It is currently an important drug in the treatment of acute myeloid leukemia. It is also active against acute lymphocytic leukemia, and to a lesser extent, is useful in chronic myelocytic leukemia and non-Hodgkin's lymphoma. The primary action of araC is inhibition of nuclear DNA synthesis. Handschumacher, R. and Cheng, Y., "Purine and Pyrimidine Antimetabolites", Cancer Medicine, Chapter XV-1, 3rd Edition, Edited by J. Holland, et al., Lea and Febigol, publishers.

5-Azacytidine is a cytidine analog that is primarily used in the treatment of acute myelocytic leukemia and myelodysplastic syndrome.

2-Fluoroadenosine-5'-phosphate (Fludara, also referred to as FaraA)) is one of the most active agents in the treatment of chronic lymphocytic leukemia. The compound acts by inhibiting DNA synthesis. Treatment of cells with F-araA is associated with the accumulation of cells at the G1/S phase boundary and in S phase; thus, it is a cell cycle S phase-specific drug. Incorporation of the active metabolite, F-araATP, retards DNA chain elongation. F-araA is also a potent inhibitor of ribonucleotide reductase, the key enzyme responsible for the formation of dATP.

2-Chlorodeoxyadenosine is useful in the treatment of low grade B-cell neoplasms such as chronic lymphocytic leukemia, non-Hodgkins' lymphoma, and hairy-cell leukemia. The spectrum of activity is similar to that of Fludara. The compound inhibits DNA synthesis in growing cells and inhibits DNA repair in resting cells.

Although a number of chemotherapeutic agents have been identified and are currently used for the treatment of cancer, new agents are sought that are efficacious and which exhibit low toxicity toward healthy cells.

U.S. Pat. Nos. 5,817,667 and 6,063,787 disclose the use of β-LOddC for the treatment of tumors, including cancer or for the treatment of psoriasis and related hyperproliferative diseases/conditions.

U.S. Pat. Nos. 5,558,736; 5,565,438; 5,587,362; and 5,567,688; relate to the use of LFMAU and certain related derivates thereof as anti-viral agents in the treatment of Hepatitis B virus and Epstein Barr virus. U.S. Pat. No. 6,894,159 relates to an alternative synthesis, of LFMAU.

OBJECTS OF THE INVENTION

Therefore, it is an object of the present invention to provide compounds and pharmaceutical compositions that exhibit anti-tumor, and in particular, anti-cancer and/or anti-hyperproliferative growth disease activity.

It is another object of the present invention to provide pharmaceutical compositions for the treatment of cancer and hyperproliferative cell growth diseases.

It is further object of the present invention to provide a method for the treatment of cancer and hyperproliferative cell growth diseases.

Any one or more of these and/or other objects of the invention may be readily gleaned from a review of the description of the invention which follows.

SUMMARY OF THE INVENTION

The present invention relates to the use of the compound according to formula I, below for the treatment of tumors, cancer and hyperproliferative diseases, among others:

Formula I

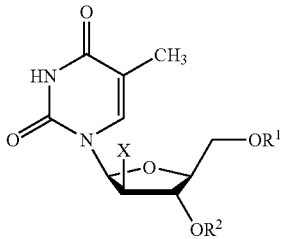

Where X is H or F;
$R^1$ and $R^2$ are independently H, an acyl group, a $C_1$-$C_{20}$ alkyl or ether group, a phosphate, diphosphate, triphosphate or a phosphodiester group, a $$\left[ \begin{array}{c} O \\ \parallel \\ Nu\text{---}P\text{---}O \\ | \\ OR^8 \end{array} \right]_k \begin{array}{c} O \\ \parallel \\ P \\ | \\ OR^8 \end{array} \quad \text{or} \quad Nu\text{---}\overset{O}{\underset{\parallel}{C}}\text{---} \text{ group;}$$

Where Nu is a radical of a biologically active compound such as an anticancer, antiviral or antihyperproliferative compound such that an amino group or hydroxyl group from said biologically active agent forms a phosphate, phosphoramidate, carbonate or urethane group with the adjacent moiety;

Each $R^8$ is independently H, or a $C_1$-$C_{20}$ alkyl or ether group, preferably a $C_1$-$C_{12}$ alkyl group; k is 0-12, preferably, 0-2; and pharmaceutically acceptable salts, solvates and polymorphs thereof. In preferred aspects of the present invention, $R^1$ is H, a $C_2$-$C_{18}$ acyl group or a phosphate group and $R^2$ is H.

Pharmaceutical compositions comprising an anti-cancer effective amount of one or more of the compounds of formula 1, optionally (and preferably) in combination with an effective amount of at least one additional anti-cancer agent as otherwise described herein and at least one carrier, additive or excipient are additional aspects of the present invention.

Further aspects of the present invention relate to methods for treating hyperproliferative diseases, including tumors, especially malignant tumors and cancer. This aspect(s} of the present invention is directed to methods of treating tumors, cancer, hyperproliferative diseases, including psoriasis, genital warts (papilloma), hyperproliferative cell growth such as abnormal cell proliferation or growth of non-transformed cells including precancerous cells, and any cell which expresses an abnormal or foreign cell surface protein or antigen. Methods for treating chronic inflammatory diseases and viral and other microbial infections alone or in combination with another agent are further aspects of the invention.

The method aspect includes treating hyperproliferative diseases including psoriasis, genital warts and hyperproliferative cell growth diseases, including hyperproliferative keratinocyte diseases such as hyperkeratosis, ichthyosis, keratoderma or lichen planus and chronic inflammatory diseases such as arthritis, including rheumatoid arthritis and osteoarthritis as well as hepatitis C virus (HCV) infections, the methods comprising administering to a patient in need thereof an effective amount of a compound according to the present invention, optionally in combination with at least one additional anti-cancer agent, antihyperproliferative agent or antiviral agent, optionally in combination with a pharmaceutically acceptable carrier, additive or excipient.

Virtually any cancer can be treated using the compositions and methods according to the present invention. Exemplary cancers which may treated include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among numerous others.

It is noted that the use of LFMAU or its derivative in the treatment of cancer exhibits little, if any, host toxicity, and when coadministered with another anti-cancer agent in the treatment of cancer in a subject, is substantially no more toxic and in certain instances, may actually exhibit less toxicity, than the other anti-cancer agent alone, which is an unexpected result. Moreover, a combination of an effective amount of one of the nucleoside compounds according to the present invention with another anticancer agent ("the other anticancer agent"), in many instances, will provide a synergistic enhancement (i.e., more than additive) of the anticancer activity of the other anticancer agent.

DETAILED DESCRIPTION OF THE INVENTION

Figure 1:
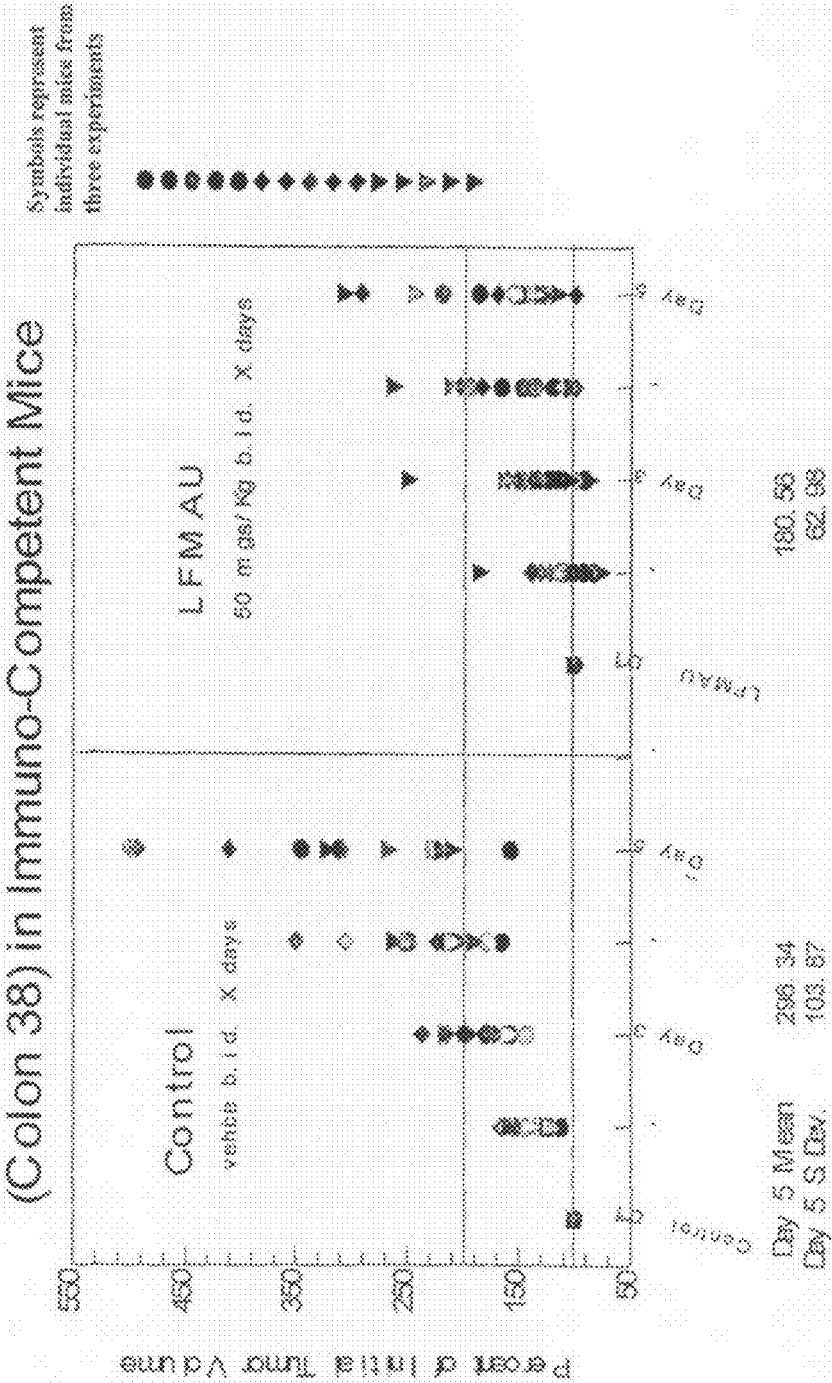
FIGS. 1-6 show the effects of LFMAU, either alone or in combination with other anti-cancer agents on tumors as indicated in the figures and the experimental section.

The term "compound", as used herein, unless otherwise indicated, refers to any specific chemical compound disclosed herein. Within its use in context, the term generally refers to a single compound preferably, L-β anomers of FMAU or its various racemic, enantiomerically enriched (to at least 75%, 85%, 95%, 98%, 99% or 99+% enantiomeric enrichment or various prodrug or derivative forms as otherwise described herein. B-L nucleoside compounds according to formula 1 which are used in the present invention are referred to generally as L-FMAU, L-dT (also, "LdT" or "LDT") or their derivatives. Compounds according to the present invention exhibit little, if any toxicity, to host cells in treating cancer, an unexpected result.

The term "effective" is used herein, unless otherwise indicated, to describe an amount of a compound which, in context, is used to produce or effect an intended result, whether that result relates to the treatment of a hyperproliferative disease state, chronic inflammatory disease, a viral infection such as a HCV infection, a tumor including a carcinogenic tumor or other cancer or the treatment of a precancerous lesion or other cell(s) which express abnormal or foreign proteins or immunogens on a cell surface. In certain aspects related to the coadministration of a compound according to the present invention with another anticancer agent, the present invention relates to the enhancement of the anti-cancer effect of another anti-cancer compound. This term subsumes all other effective amount or effective concentration terms which are otherwise described in the present application. With respect to an anti-cancer effect, that effect may be one or more of inhibiting further growth of tumor or cancer cells, reducing the likelihood or eliminating metastasis or producing cell death in the tumor or cancer cells, resulting in a shrinkage of the tumor or a reduction in the number of cancer cells or preventing the regrowth of a tumor or cancer after the patient's tumor or cancer is in remission. As indicated, LFMAU, LDT or their derivatives may exhibit an anti-cancer effect alone and/or may enhance the ability of another anti-cancer agent to exhibit an anti-cancer effect in an additive or synergistic manner (i.e., more than additive). In the case of anticancer effective amounts, the amounts of active agent used may be as much as twice, three times, five times or even ten times or more the amount used to treat antiviral infections/indications. This is due to the fact that in treating cancer, the patient may be able to tolerate much higher amounts of drug, which are not recommended for use to treat antiviral indications, because toxicity may become more of an issue at higher concentrations (even though the compounds are relatively low in toxicity).

The term "patient" or "subject" is used throughout the specification to describe an animal, generally a mammal and preferably a human, to whom treatment, including prophylactic treatment, with the compositions according to the present invention is provided. For treatment of those infections, conditions or disease states which are specific for a specific animal such as a human patient, the term patient refers to that specific animal.

The term "pharmaceutically acceptable salt" is used throughout the specification to describe a salt form of one or more of the compositions (and in particularly preferred aspects according to the present invention, phosphate salts) herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of neoplasia, including cancer, the term "salt" shall mean a pharmaceutically acceptable salt, solvate or polymorph consistent with the use of the compounds as pharmaceutical agents.

The term "pharmaceutically acceptable derivative" or "derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "alkyl" shall mean within its context a $C_1$-$C_{20}$, preferably a $C_1$-$C_{10}$ linear, branch-chained or cyclic fully saturated hydrocarbon radical, which may be optionally substituted, such as with a phenyl group, for example. The term "ether" shall mean a $C_1$ to $C_{20}$ ether group, formed from an oxygen and an alkyl group at a position on the sugar moiety of compounds according to the present invention, and preferably contains at least one oxygen group within the alkyl chain. The term alkyl shall also embrace aralkyl groups such as benzyl groups, which phenyl group may be optionally substituted.

The term "acyl" is used throughout the specification to describe a group at the 5' or 3' position of the nucleoside analog (i.e., at the free hydroxyl position in the sugar synthon) which contains a $C_1$ to $C_{20}$ linear, branched or cyclic alkyl chain or a related group as otherwise described herein. The acyl group at the 5' or 3' position ($R^1$ or $R^2$), in combination with the corresponding hydroxyl group results in an ester, which, after administration, may be cleaved to produce the free nucleoside form of the present invention. Acyl groups according to the present invention may be represented by the structure:

where $R_4$ is a $C_1$ to $C_{20}$ linear, branched or cyclic alkyl group, alkoxyalkyl, aryloxyalkyl, such as phenoxymethyl, aryl, alkoxy, all of which may be optionally substituted, among others. Preferred acyl groups are those where $R_4$ is a $C_1$ to $C_{10}$ alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, amino acids, among numerous others including certain pharmaceutically acceptable sulphonate groups, which are also considered acyl groups for purposes herein. One of ordinary skill in the art will recognize the acyl groups which will have utility in the present invention, either to synthesize the target pharmaceutical compounds or as prodrug forms of the nucleosides according to the present invention.

The term "phosphate ester" or "phosphodiester" is used throughout the specification to describe mono-phosphate groups at the 5' or 3' position of the ribose moiety or sugar synthon (preferably, on the 5' position) which are diesterified such that the phosphate group is rendered neutral, i.e., has a neutral charge. Phosphate esters for use in the present invention include those represented by the structures:

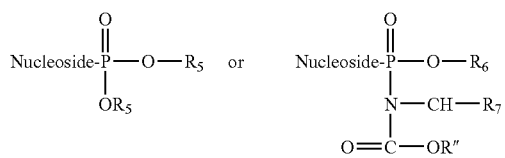

where $R_5$, $R_6$ and R" are selected from a $C_1$ to $C_{20}$ linear, branched or cyclic alkyl group, alkoxyalkyl, aryloxyalkyl, such as phenoxymethyl, aryl and alkoxy, among others, and $R_7$ is a $C_1$ to $C_{20}$ linear, branched or cyclic alkyl or acyl group, alkoxyalkyl, aryloxyalkyl, such as phenoxymethyl, aryl and alkoxy, among others. Preferred monophosphate esters for use in prodrug forms according to the present invention are those where $R_5$ is a $C_1$ to $C_{20}$ is a linear or branched chain alkyl group, more preferably a $C_1$ to $C_3$ alkyl group.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention.

The term "tumor" is used to describe a malignant or benign growth or tumefacent.

The term "hyperproliferative disease state" refers to a disease state in which cells are growing in an uncontrolled manner, whether that growth is cancerous or not. Such a disease state may be reflected in psoriasis, genital warts or other hyperproliferative cell growth diseases, including hyperproliferative keratinocyte diseases including hyperkeratosis, ichthyosis, keratoderma or lichen planus, all of which disease states may be treated using compounds according to the present invention. "Antihyperproliferative" refers to the fact that a compound acts to treat hyperproliferative disease states or conditions hereunder. Anticancer compounds with very low or no toxicity are also considered antihyproliferative compounds hereunder.

The term "anti-cancer compound" or "anti-cancer agent" is used to describe any compound (including its derivatives) which may be used to treat cancer. Anti-cancer compounds for use in the present invention may be co-administered with one or more of L-FMAU or its derivatives for the effect that L-FMAU or its derivative compounds have on enhancing the effect of the anti-cancer compound in treating cancer in a patient pursuant to the present invention. In many instances the co-administration of L-FMAU or its derivative and another anti-cancer compound results in a synergistic anti-cancer effect. Exemplary anti-cancer compounds for use in the present invention for co-administration with L-FMAU or its derivative include anti-metabolites agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and ABL kinase inhibitors (e.g. gleevec or imatinib). Anti-cancer compounds for use in the present invention include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

The term "bioactive agent" includes any biologically active agent, including a prodrug form of the active agent, which can be administered in combination with LFMAU or LDT or a derivative (such as a prodrug form) pursuant to the present invention and can include active agents or their derivatives which form dual acting agents wherein the bioactive agent or its derivative and the nucleoside compounds or its derivative (referred to collectively as conjugates) are chemically linked as otherwise described herein. In addition to anticancer agents as otherwise described above, bioactive agents may include a number of antiviral agents including for example, the following agents, which are useful for the treatment of HIV, HBV and other viral infections as well as agents which treat hyperproliferative diseases and chronic inflammatory diseases such as arthritis, including rheumatoid arthritis and osteoarthritis, among numerous others.

In addition to the anticancer agents described above, exemplary bioactive agents which may be chemically linked to LFMAU or LDT or a derivative as described herein include for example, Atazanavir (BMS-232632) using the free secondary hydroxyl group;
Bis(POM)-PMEA (Adefovir dipivoxyl) using the free amine group;
Bis(POC)-PMPA (Tenofovir disoproxil) using the free amine group;
Etecavir using the primary hydroxyl group on the carbocyclic sugar synthon;
Indinavir (Crixivan, MK-639 L-735,524 from Merck) using the free secondary hydroxyl group;
KHI-227 (Kynostatin of Nikko Kyodo Co.) using the free secondary hydroxyl group:
2-[3-[3-(S)-[[(Tetrahydrofuranyloxy)carbonyl]amino]-4-phenyl-2(R)-hydroxybutyl]]-N-(1,1-dimethylethyl) decahydro-3-isoquinolinecarboxamide (IsoquinCON furanyl urethane analog from Merck) using the free secondary hydroxyl group;
Carbamic acid, [3-{[(4-methoxyphenyl)sulfonyl](cyclopenylmethyl)amino]-2-hydroxy-1-(phenylmethyl)propyl]-, tetrahydrofuranyl ester (VB-11,328 of Vertex) using the free secondary hydroxyl group;
KNI-174 from Nikko Kyodo Co. using the free secondary hydroxyl (or free amine) group;
Val-Val-Sta from Sandoz (Austria) using the free secondary hydroxyl group;
CPG53820 from Ciba-Geigy using the free secondary hydroxyl group;
bis-Val HOEt-N2 aza-peptide isostere using the free secondary hydroxyl group;
C2-Sym Phosphinic amide derivative from Hoechst AG using the free amine group;
2,5-Diamino-N,N'-bis(N-benzyloxycarbonyluelyl)-1,6-diphenyl-3(S),4(S)-hexanediol BzOCValPhe[diCHOH (SS)PheValBzOC from Abbott using the free secondary hydroxyl group;
2,5-Diamino-N,N'-bis(N-benzyloxycarbonyluelyl)-1,6-diphenyl-3(R),4(R)-hexanediol BzOCValPhe[diCHOH (RR)PheValBzOC from Abbott using the free secondary hydroxyl group;
bis(S-acetyl-2-thioethyl)phosphotriester of ddA or [bis(SATE)ddAMP] using the free amine;
BILA 2186 BS (Bio-Mega/Boehringer Ingelheim) using the free secondary hydroxyl group;
Agenerase (Amprenavir; VX-478; 141W94) of Vertex/Kissei/Glaxo Wellcome at the free secondary hydroxyl or amine group;
A-98881 (Azacyclic urea derivative) of Abbott using the free secondary hydroxyl group or phenolic hydroxyl group;
A-83962 (Rifonavir derivative) of Abbott using the free secondary hydroxyl group;
A-80987 (Rifonavir derivative) of Abbott using the free secondary hydroxyl group;
(2-Naphthylcarbonyl)Asn[decarbonylPhe-hydroxyethyl] ProOtertButyl or 2NaphCOAsnPhe[CHOHCH2]Pro-OtBu of Roche using the free secondary hydroxyl;
2-Aminobenzylstatine Valyl Cbz derivative of Sandoz using the free secondary hydroxyl or amine;
2-Aminobenzylstatine Valyl Cbz derivative of Sandoz using the free hydroxyl;
10H-2(Cbz-ValNH)3PhPr [14]paracyclophane derivative of Sandoz using the free secondary hydroxyl;
10H-2(Cbz-ValNH)3PhPr [13]paracyclophane derivative of Sandoz using the free secondary hydroxyl;
10H-2(Cbz-ValNH)3PhPr [13]metacyclophane derivative of Sandoz using the free secondary hydroxyl;
10H-2(Cbz-Tle)3PhPr [14]paracyclophane derivative of Sandoz using the free secondary hydroxyl;
1-(2OHPr)-4-substituted-piperazine (cyclopropyl), thienyl carbamate deriv. (from Merck) using the free secondary hydroxyl group;
1-(2OHPr)-4-substituted-piperazine (cyclobutyl), thienyl carbamate derive. (from Merck) using the free secondary hydroxyl group;
1-(2OHPr)-4-substituted-piperazine (3-pentyl), thienyl carbamate derive. (from Merck) using the free secondary hydroxyl group;
10H-2(Cbz-ValNH)3PhPr[17]paracyclophane derivative (from Sandoz) using the free second hydroxyl group;
A-81525 (from Abbott) using the free secondary hydroxyl group;
XM323 (DMP-323 from DuPont Merck) using the free primary or secondary hydroxyl groups;
Tipranavir (U-140690 or PHU-140690 from Pharmacia & Upjohn) using the phenolic hydroxyl group;
ThienopyridCON thienyl urethane derivatives (HOCH2CH2 isostere from Lilly) (the benzyl substituted derivative or the methyl mercaptophenyl substituted derivatives) using the free secondary hydroxyl groups;
SDZ PRI 053 (Sandoz) using the free secondary hydroxyl group;
SD146 (DuPont Merck) using either of the free secondary hydroxyl groups;
Telinavir (SC-52151 from Searle/Monsanto) using the free secondary hydroxyl group or amine;
(R)2QuinCOAsnPhe[CHOHCH2]PipCONHtBu (from Roche) using the free secondary hydroxyl group or amine;
Saquinavir (Invirase or RO 31-8959 from Roche) using the free secondary hydroxyl group or amine;
Saquinavir/Melfinavir derivative (from Lilly) using the free secondary hydroxyl group;
IsoquinCON Thf-Thf Urethane Analog (from Merck) using the free secondary hydroxyl group;
IsoquinCON thienyl urethane analog (from Merck) using the free secondary hydroxyl group;
R-87366 (AHPBA analog from Sankyo) using the free amine group;
DMP 460 (Dupont Merck/Avid) using the free secondary hydroxyl groups or either of the aniline amine groups;
L685,434 (Merck) using the free secondary hydroxyl group;
L685,434-6-Hydroxyl derivative (Merck) using the free secondary hydroxyl group;
L685,434-OEtNMe2 (Merck) using the free secondary hydroxyl group;

L685,434-OPrMorph derivative (Merck) using the free secondary hydroxyl group;

L689,502 (Merck) using the free secondary hydroxyl group;

Lasinavir (CGP 61755 from CIBA/Novartis) using the free secondary hydroxyl group;

Aluviran (Lopinavir, ABT-378, RS-346 A157378 of Abbott) using the free secondary hydroxyl group;

Nelfnavir-octahydro-thienopyridine analog (from Lilly) using the free secondary hydroxyl group;

P9941 (from DuPont Merck) using either of the free secondary hydroxyl groups;

Palinavir (BILA 2011 BS from BIO-MEGA/Boehringer Ingelheim) using the free secondary hydroxyl group;

Penicillin, 2Isoquin-OHPrNH2 analog (from Glaxo Wellcome) using the free secondary hydroxyl group, among numerous others.

The above active compounds, and other relevant bioactive agents for use in the dual antagonist aspect of the present invention may be found at the NIH website at http://www.niaid.nih.gov/daids/dtpdb/, relevant portions of which are incorporated by reference herein.

The term "coadministration" or "combination therapy" is used to describe a therapy in which at least two active compounds in effective amounts are used to treat cancer or another disease state or condition as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more anti-cancer agent, including antimetabolites, alkylating agents, topoisomerase I and topoisomerase II inhibitors as well as microtubule inhibitors, among others. Anticancer compounds for use in the present invention include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileulin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogen mustard); megestrol acetate; melphalan (L-PAM); mercaptopurine (6-MP), mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others. Coadministration of one of the present nucleoside compounds with another anticancer agent will often result in a synergistic enhancement of the anticancer activity of the other anticancer agent, an unexpected result. One or more of the present nucleoside compounds may also be coadministered with another bioactive agent (e.g., antiviral agent, antihyperproliferative disease agent, agents which treat chronic inflammatory disease, among others as otherwise described herein).

The present invention includes the compositions comprising the pharmaceutically acceptable salts of compounds of the present invention. The acids which are used to prepare the pharmaceutically acceptable acid addition salts of the aforementioned compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among others.

The invention also includes compositions comprising base addition salts of the present compounds. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e, calcium and magnesium), ammonium or water-soluble amine addition salts such as N-methylglucamine-(meglumine), and the lower alkanolammonium and other base salts of pharmaceutically acceptable organic amines, among others.

The compounds of this invention primarily related to nucleoside compounds which are characterized as β-L nucleosides, but can include other stereoisomers where relevant, including optical isomers of the present compounds, as well as racemic, diastereomeric and other mixtures of such isomers, as well as all polymorphs of the compounds.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.5 milligram to about 750 milligrams, more preferably about 1 milligram to about 600 milligrams, and even more preferably about 10 milligrams to about 500 milligrams of active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Other aspects of the present invention are directed to methods of treating tumors, cancer, precancerous cells and lesions, cells which express abnormal or foreign surface proteins or antigens, psoriasis, genital warts (papilloma), chronic inflammatory diseases such as arthritis, rheumatoic arthritis and osteoarthritis, hyperproliferative cell growth diseases, including hyperproliferative keratinocyte diseases such as hyperkeratosis, ichthyosis, keratoderma or lichen planus and HCV the method comprising administering to a patient in need of treatment thereof an effective amount of a compound according to the formula:

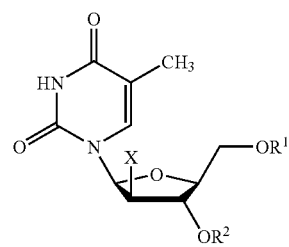

Where X is H or F;
$R^1$ and $R^2$ are independently H, an acyl group, a $C_1$-$C_{20}$ alkyl or ether group, a phosphate, diphosphate, triphosphate or a phosphodiester group, a

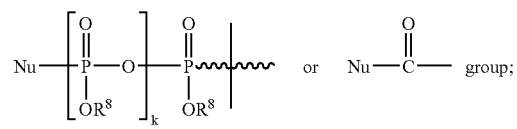

group;

Where Nu is a radical of a biologically active compound such as an anticancer, antiviral or antihyperproliferative compound such that an amino group or hydroxyl group from said biologically active agent forms a phosphate, phosphoramidate, carbonate or urethane group with the adjacent moiety; Each $R^8$ is independently H, or a $C_1$-$C_{20}$ alkyl or ether group, preferably a $C_1$-$C_{12}$ alkyl group; k is 0-12, preferably, 0-2; and pharmaceutically acceptable salts thereof. In preferred aspects of the present invention, the above compound is co-administered with at least one additional anti-cancer agent or agent which is effective against hyperproliferative cell growth diseases. In other preferred aspects of the present invention, $R^1$ is H, a $C_2$-$C_{18}$ acyl group or a phosphate group and $R^2$ is H.

Specific examples of pharmaceutically acceptable derivatives of LFMAU or LDT include, but are not limited to: compounds wherein $R^1$ and $R^2$ are independently selected from the group consisting of alkyl and acyl, specifically including but not limited to methyl, ethyl, propyl, butyl, pentyl, hexyl, isopropyl, isobutyl, sec-butyl, t-butyl, isopentyl, amyl, t-pentyl, 3-methylbutyryl, hydrogen succinate, 3-chlorobenzoate, cyclopentyl, cyclohexyl, benzoyl, acetyl, pivaloyl, mesylate, propionyl, butyryl, valeryl, caproic, caprylic, capric, lauric, myristic, palmitic, stearic, oleic, and amino acids including but not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl, and wherein one of $R^1$ and $R^2$ can be H.

LFMAU, LDT or their derivatives can be provided in the form of pharmaceutically acceptable salts. As used herein, the term pharmaceutically acceptable salts or complexes refers to salts or complexes of LFMAU and/or LDT that retain the desired biological activity of the parent compound and exhibit minimal, if any, undesired toxicological effects. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

Modifications of the active compound, specifically at the 5'-O and 3'-O positions, can affect the solubility, bioavailability and rate of metabolism of the active species, thus providing control over the delivery of the active species. Further, the modifications can affect the anticancer activity of the compound, in some cases increasing the activity over the parent compound. This can easily be assessed by preparing the derivative and testing its anticancer activity according to the methods described herein, or other method known to those skilled in the art.

Preparation and Administration of the Active Compounds and Compositions

LFMAU or its derivatives can be prepared according to the methods disclosed in detail in one or more of U.S. Pat. Nos. 5,565,438; 5,808,040; 6,894,159; 5,558,736; 5,587,362; and 5,567,688; relevant portions of which are incorporated by reference herein, or by any other method known to those skilled in the art. LDT or its derivatives may be readily made using methods well known in the art. In the case of compounds which contain two active agents, linking of LFMAU or LDT or its derivatives to another active agent may be readily accomplished following standard techniques. Appropriate blocking groups aid agents to form the linking groups may be used readily.

Humans, equines, canines, bovines and other animals, and in particular, mammals, suffering from cancer can be treated by administering to the patient (subject) an effective amount of LFMAU, LDT or its derivative, including a pharmaceutically acceptable salt thereof optionally in a pharmaceutically acceptable carrier or diluent, either alone, or in combination with other known anticancer or pharmaceutical agents. This treatment can also be administered in conjunction with other conventional cancer therapies, such as radiation treatment or surgery.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier.

The compound is conveniently administered in any suitable unit dosage form, including but not limited to one containing 1 to 3000 mg, preferably 5 to 500 mg of active ingredient per unit dosage form. An oral dosage of about 25-250 mg is usually convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, antibiotics, antifungals, antiinflammatories, or antiviral compounds. In preferred aspects of the invention, LFMAU, LDT or their derivatives are coadministered with another anticancer agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachidoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Biological Activity

A wide variety of biological assays have been used and are accepted by those skilled in the art to assess anti-cancer activity of compounds. Any of these methods can be used to evaluate the activity of the compounds disclosed herein.

One common method of assessing activity is through the use of the National Cancer Institute's ("NCI") test panels of cancer cell lines. These tests evaluate the in vitro anti-cancer activity of particular compounds, and provide predictive data with respect to the use of tested compounds in vivo. Other assays include in vivo evaluations of the compound's effect on human or mouse tumor cells implanted into or grafted onto nude mice.

EXAMPLES

In these examples, the subject of the present invention, LFMAU and/or LDT is used to determine the effect on tumor growth in a number of strains of mice.

In general, the following protocol was used to implant mice with tumor cell lines and to test drugs for the anti-cancer effect.

Passage of Colon 38:

This tumor is passed from a solid tumor growing in mice. Several grams (assuming a gram per ml) are pressed through a sterile screen and suspended in a tissue culture media without phenol red or fetal calf serum (a balanced salt solution) at 2 ml/gram of tumor. Then 0.1 ml of this tumor suspension is implanted into the flank of the mouse. Ten days to two weeks after implantation (when the tumors could be measured with a caliper), unless otherwise indicated, the drug therapy was initiated.

Implantation of Human HepG2:

This is a human hepatocarcinoma that is grown in tissue culture as a monolayer in MEM with 10% FBS. Several flasks of cells are grown, then harvested with pancreatin and resuspended in a balanced salt solution at $10^8$ per ml the 0.1 ml of this suspension is implanted into the flank of a NCR nude mouse (T cell deficient to grow human tissues). Then approximately 10 days later, when the tumor was measurable, the drug treatment started.

In general, drugs are delivered at a rate of 0.1 ml per 10 grams of body weight. Every day the mice are weighed to deter the amount to be injected and as a index of toxicity.

The Tumor Volume is calculated from the measurements by the formula: length (mm)×width (mm)×width (mm)×$\Pi$/6 (as a % of Day 1).

Experiment 1

This experiment was designed to determine the effect of LFMAU on the growth of mouse tumor (colon 38) in immuno-competent mouse. FIG. 1 indicates that LFMAU slows down the growth of colon 38 mouse tumor in immuno-competent mice. The experiment evidenced that 14 of 15 mice in the control group had their tumor size double in 5 days, whereas only 5 of 15 mice in the LFMAU treat group had their tumor size double.

Experiment 2

Figure 2:
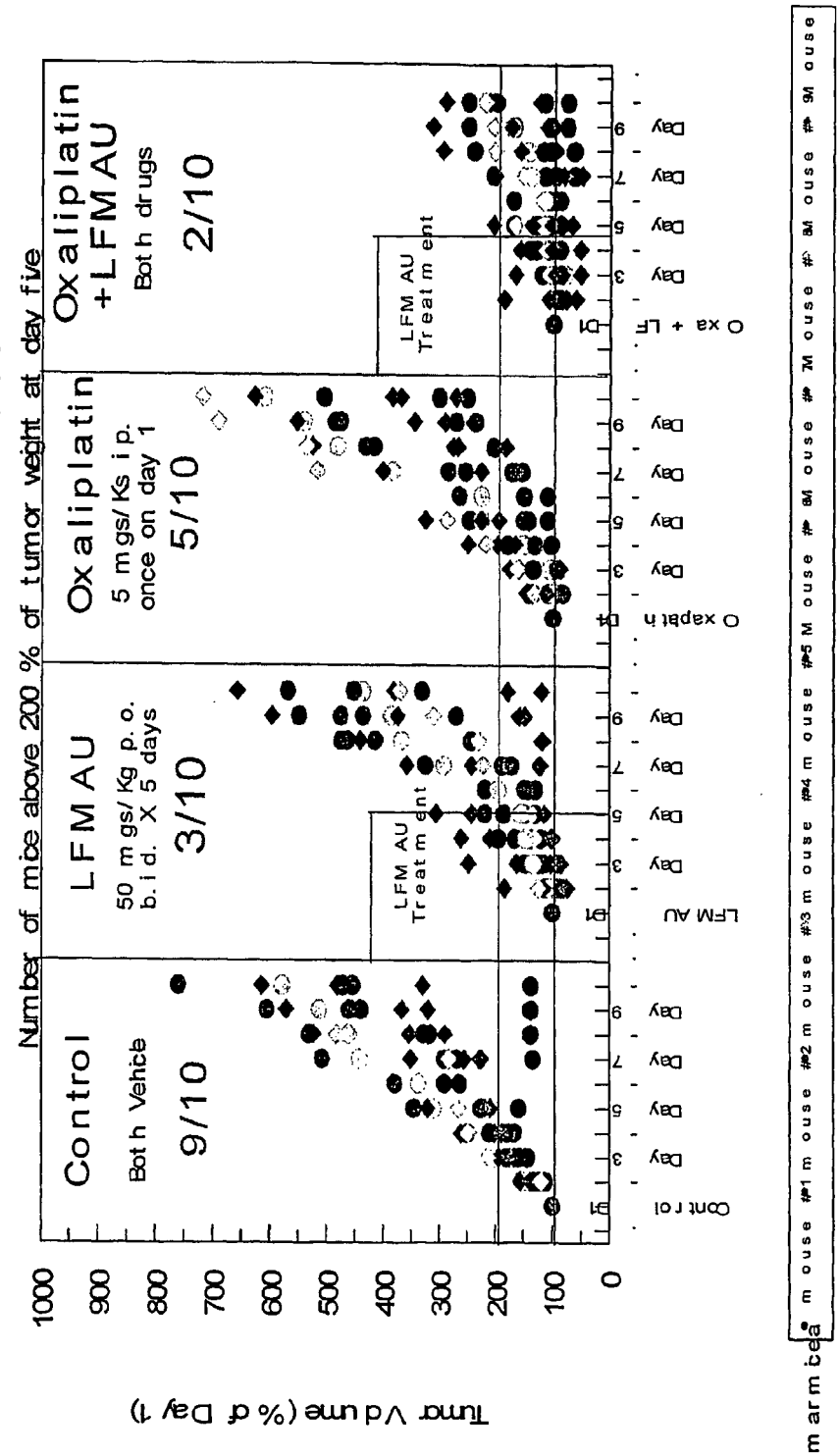

Experiment 2 tested the effects of LFMAU on the enhancement of anti-cancer drug effect (oxiplatin) on colon 38 growth in BDF1 female mice. FIG. 2 shows the results of the experiment, where LFMAU clearly enhanced the anti-tumor effect of Oxaliplatin on colon 38. The effect lasts well after the LFMAU treatment is stopped.

Experiment 3

Figure 3:
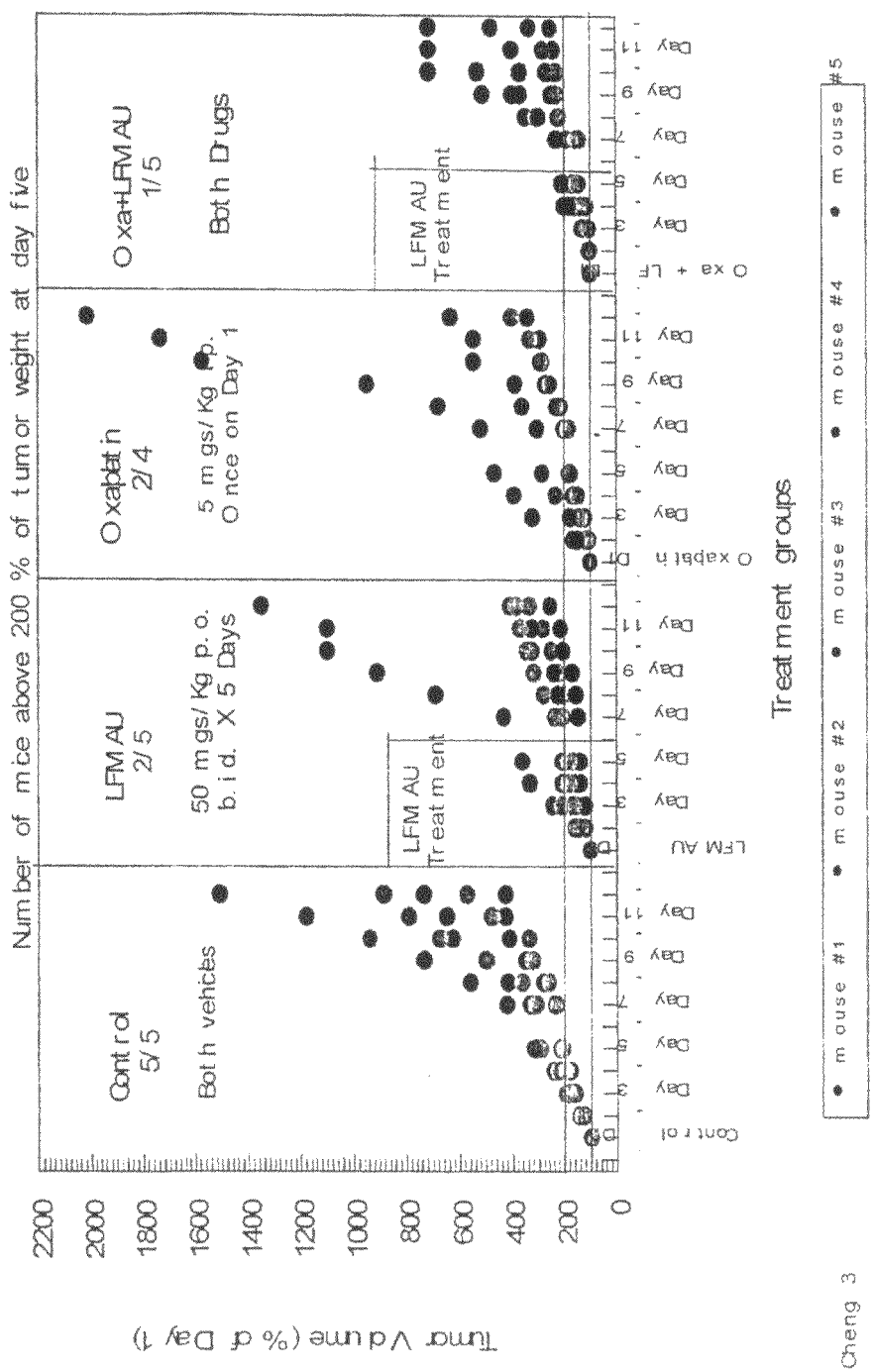

Experiment 3 tested the effects of LFMAU on the enhancement of anti-cancer drug effect (oxiplatin) on colon 38 growth into NCR Nu/Nu mice. FIG. 3 shows the results of the experiment, where LFMAU clearly enhanced the anti-tumor effect of Oxaliplatin on colon 38 in nude mice. This experiment indicates that the action of LFMAU is probably not a T cell phenomenon. The effect lasts well after the LFMAU treatment is stopped.

Experiments 4 and 5

Figure 4:
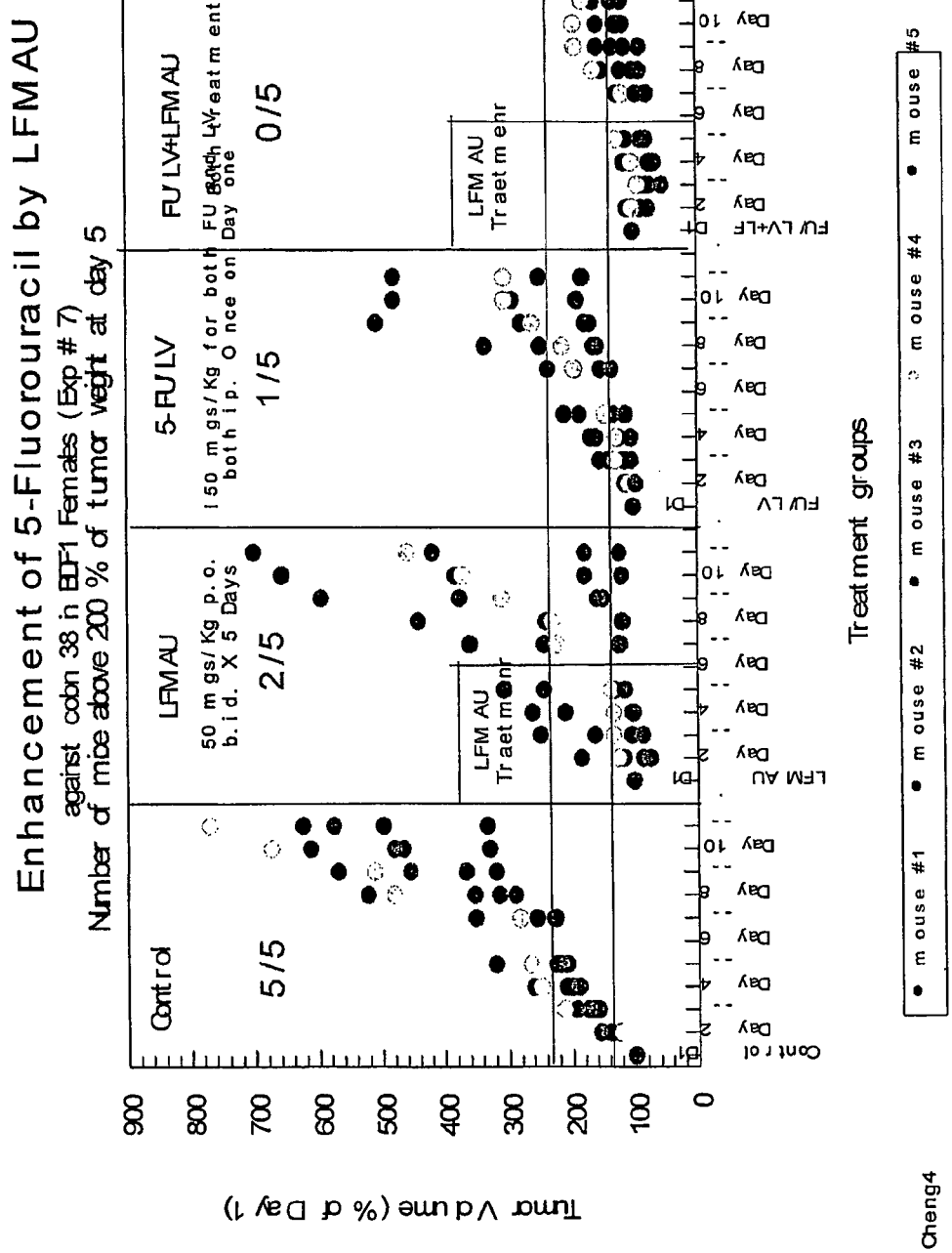
Figure 5:
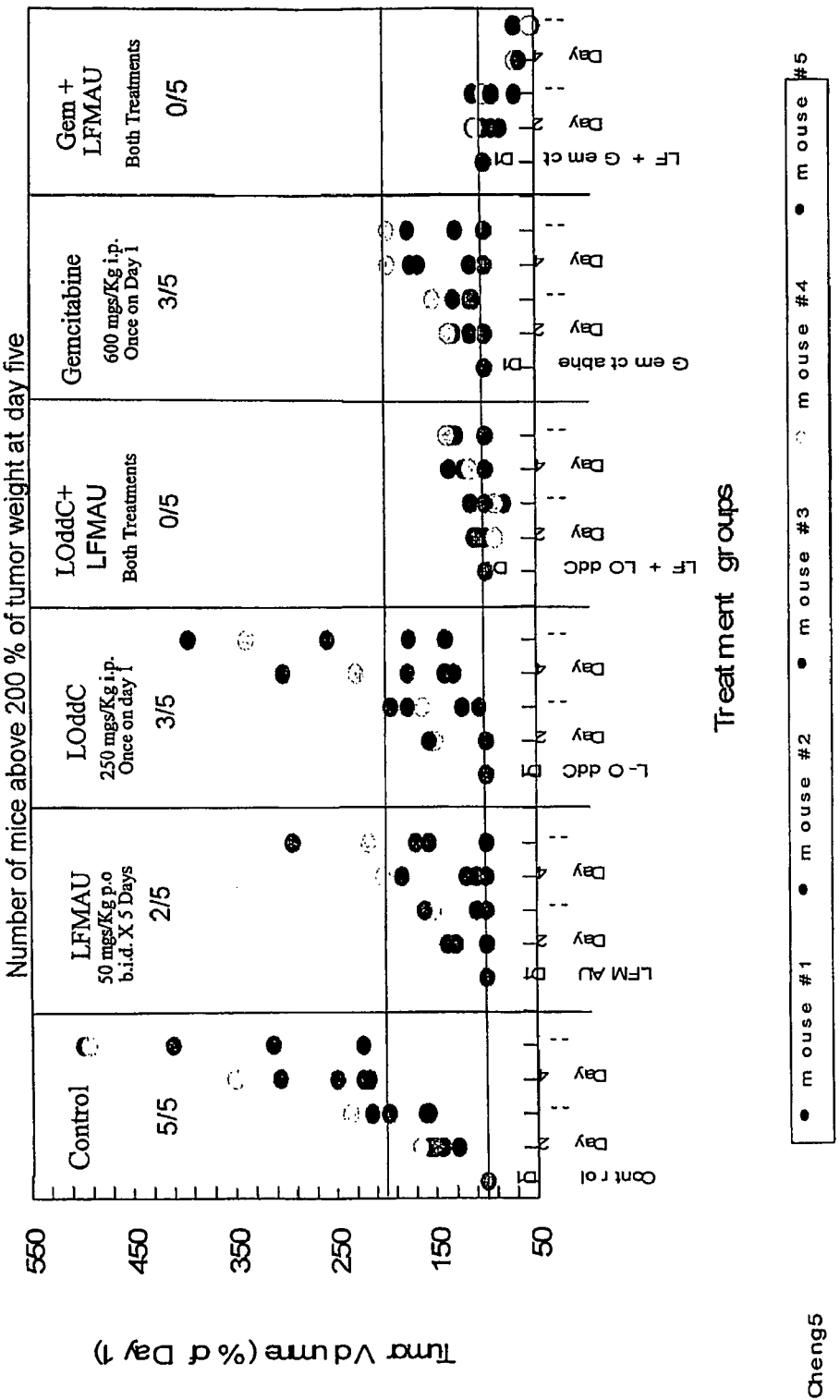

The anti-tumor enhancement effect of LFMAU with oxaliplatin was tested for other classes of anti-cancer agents. This experiment tested the effects of LFMAU on the enhancement of FU (a halogenated uracil), Gemcitabine (a D nucleoside analog) and LOddC (an L nucleoside analog) on colon 38 in BCF1 female mice. FIGS. 4 and 5 show the results of the experiment, where LFMAU clearly increased the anti-cancer effect of FU, LOddC and Gemcitabine. In the case of FU, the effect of LFMAU lasts well after the LFMAU treatment was stopped. In the case of LOddC, LFMAU enhances the anti-cancer effect and with Gemcitabine, LFMAU decreases the volume of the tumor to below its starting level on day 1.

Experiments 6

These experiments includes B16 melanoma which was injected subcutaneously into C57 BL6 mice which were pretreated for 5 days with LFMAU (B.I.D.) and then subsequently for ten days with LFMAU (B.I.D.) at 50 mg/kg. with no other anti-cancer compound. This experiment yielded tumor size S.D. for the Controls of 831±474.5 and for the LFMAU treated mice of 160±150.3. The LFMAU clearly showed an anticancer effect on B156 melanoma.

Figure 6:
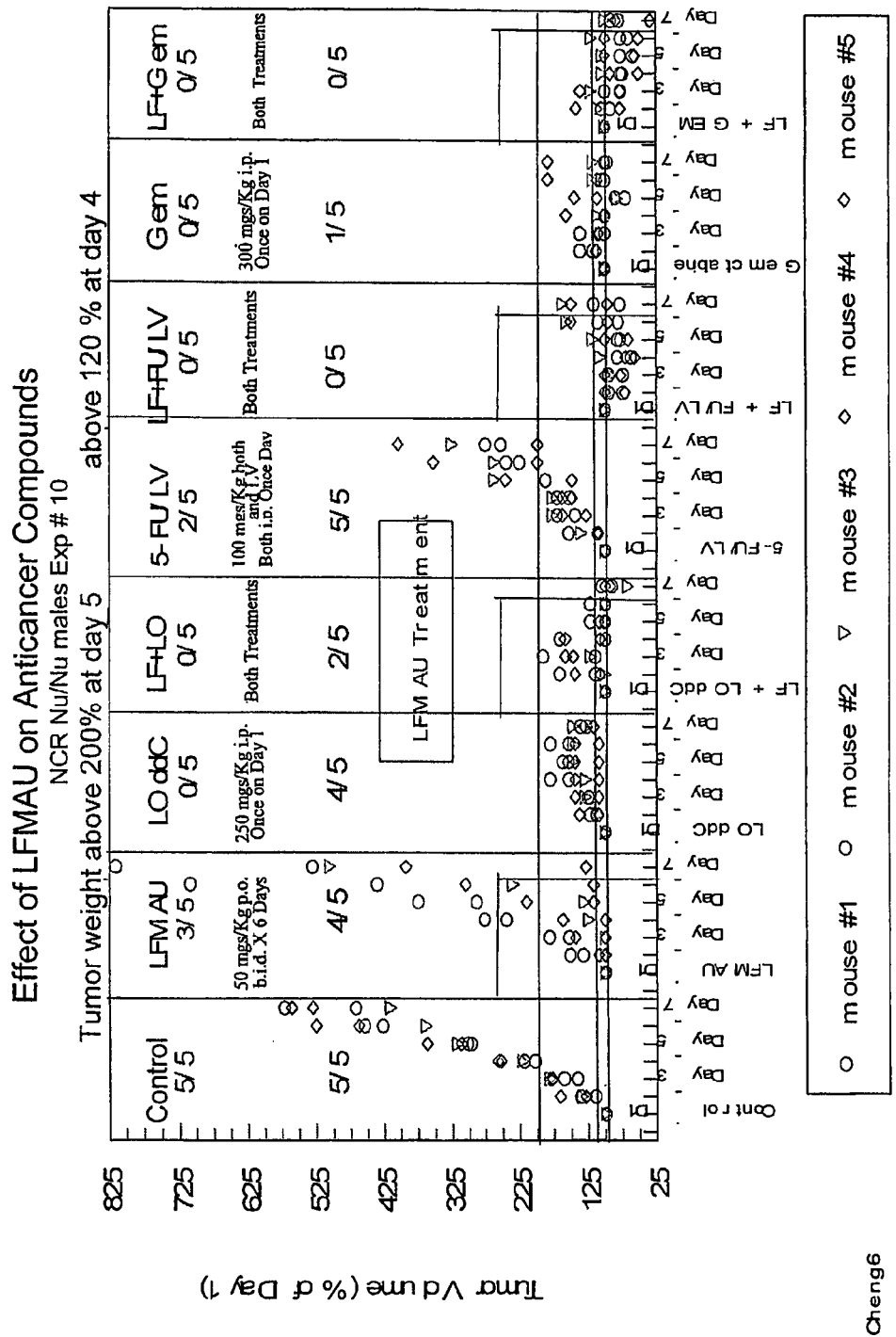

As a separate experiment, the effect of LFMAU on human tumors was tested, this time by implanting in to NCR Nu/Nu mice (Nude mice) to test the effects of LFMAU alone or in combination with other anti-cancer agents (FIG. 6). The experiment showed that LFMAU is effective against the human tumor and when combined with other anti-cancer drugs, showed that effect was enhanced, in some instances to below the day 1 starting tumor volumes.

Experiment 7

This experiment was designed to determine the effect of LDT and LFMAU alone and in combination with 5-Fluorouracil with leucovorin rescue on the growth of mouse tumor (colon 38) in immuno-competent mice. The drugs were administered to the mice according to the following schedule:

Control—vehicle only;
5FU/LV—150 mg/kg each i.p. once on day one
LDT—100 mg/kg p.o. b.i.d. for 5 days
LFMAU—50 mg/kg p.o. bid for 5 days
Combination groups received both treatments as per above schedules.

Figure 7:
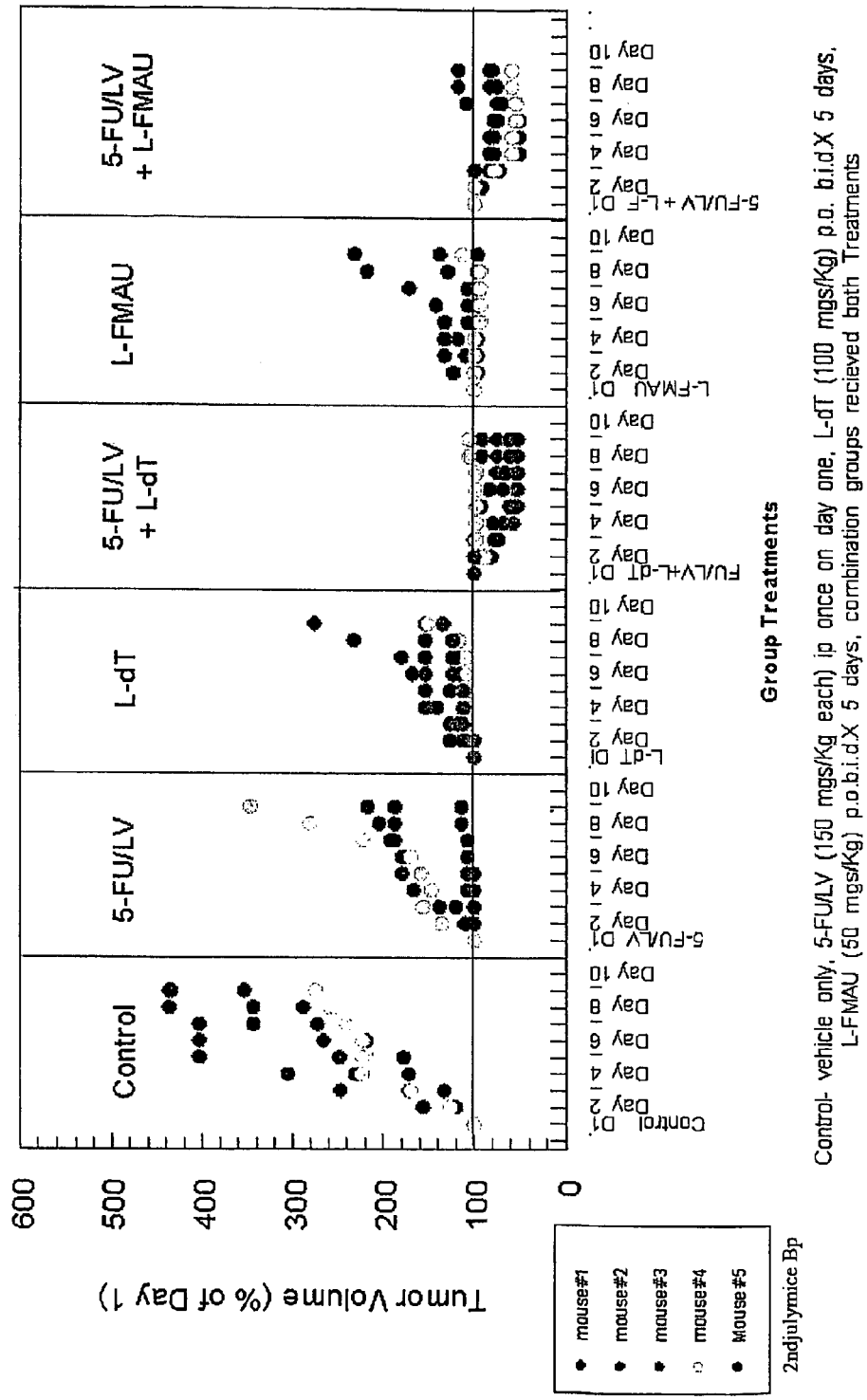
FIGS. 7-9 show the effects of L-dT and LFMAU or L-dT either alone or in combination with other anti-cancer agents as indicated in the figures and the experimental section.

FIG. 7 indicates that LDT (L-dT) and LFMAU slows down the growth of colon 38 mouse tumor in immunocompetent mice. The effect lasted well past the 5 day therapy. In each instance the effect of each of these nucleoside analogs on the anti-cancer activity of 5-FU/LV was significant (additive or synergistic).

Experiment 8

Figure 8:
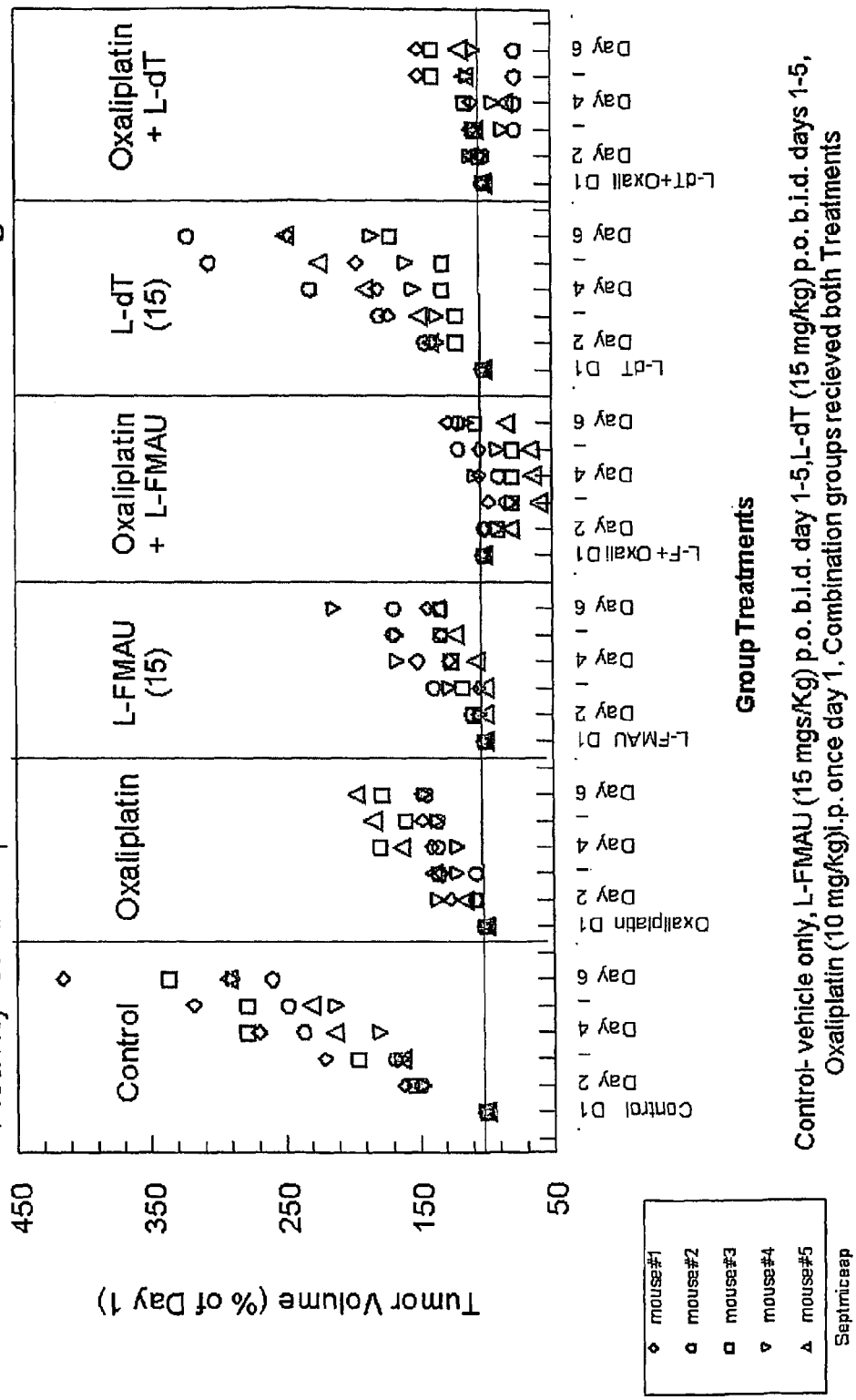

Experiment 8 tested the effects of LDT (L-dT) and LFMAU (15 mg/kg of each, same schedule as above) on the enhancement of anti-cancer drug effect (oxaliplatin 10 mg/kg i.p., once on day 1) on colon 38 growth in C57BL6 female mice. FIG. 8 shows the results of the experiment, where each of LDT and LFMAU clearly enhanced the anti-tumor effect of Oxaliplatin on colon 38 (additive or synergistic). The effect lasts well after the nucleoside treatment is stopped.

Experiment 9

Figure 9:
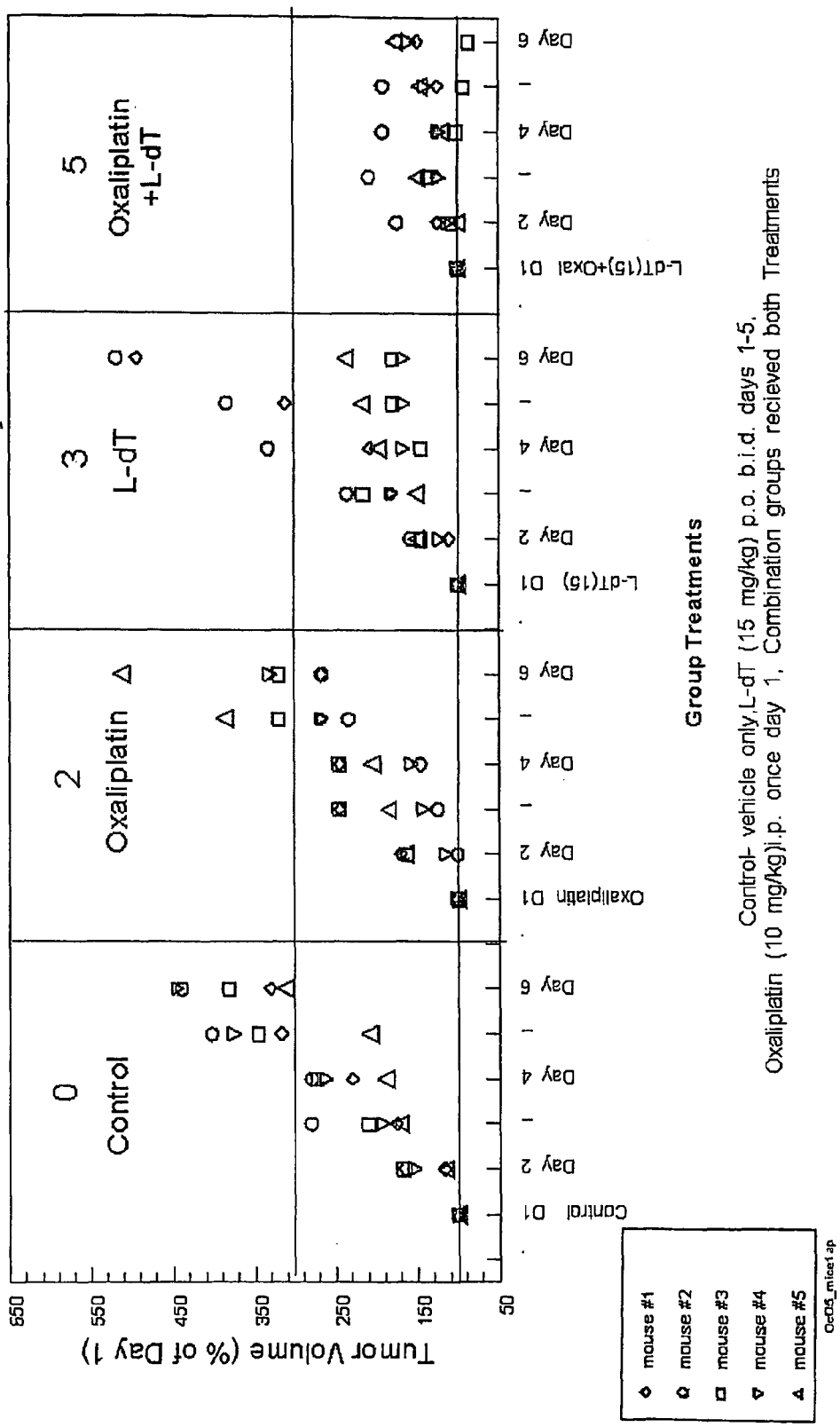

Experiment 9 tested the effects of LDT (15 mg/kg, same schedule as above) on the enhancement of anti-cancer drug effect (oxaliplatin 10 mg/kg i.p., once on day 1) on HepG2 in immunodeficient NCR Nu/Nu male mice. FIG. 9 shows the results of the experiment, where LDT was effective alone or in combination with oxaliplatin and clearly enhanced the anti-tumor effect of Oxaliplatin on HepG2 (additive or synergistic). The effect lasts after the nucleoside treatment is stopped.

Experiment 10

Figure 10:
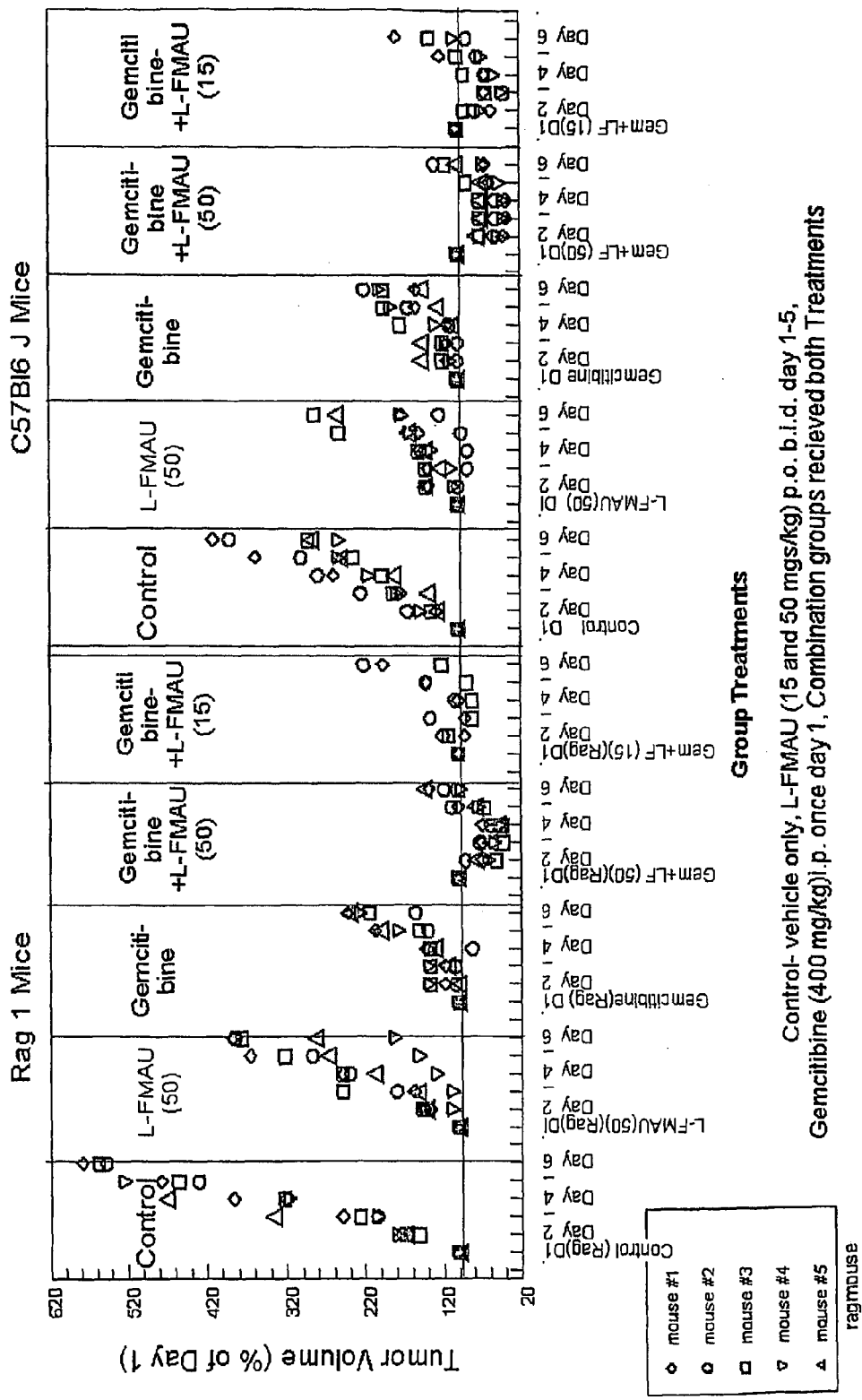
FIGS. 10-12 show the effects of LFMAU alone an in combination with gemcitabine on colon tumor growth in Rag 1 mice.
Figure 11:
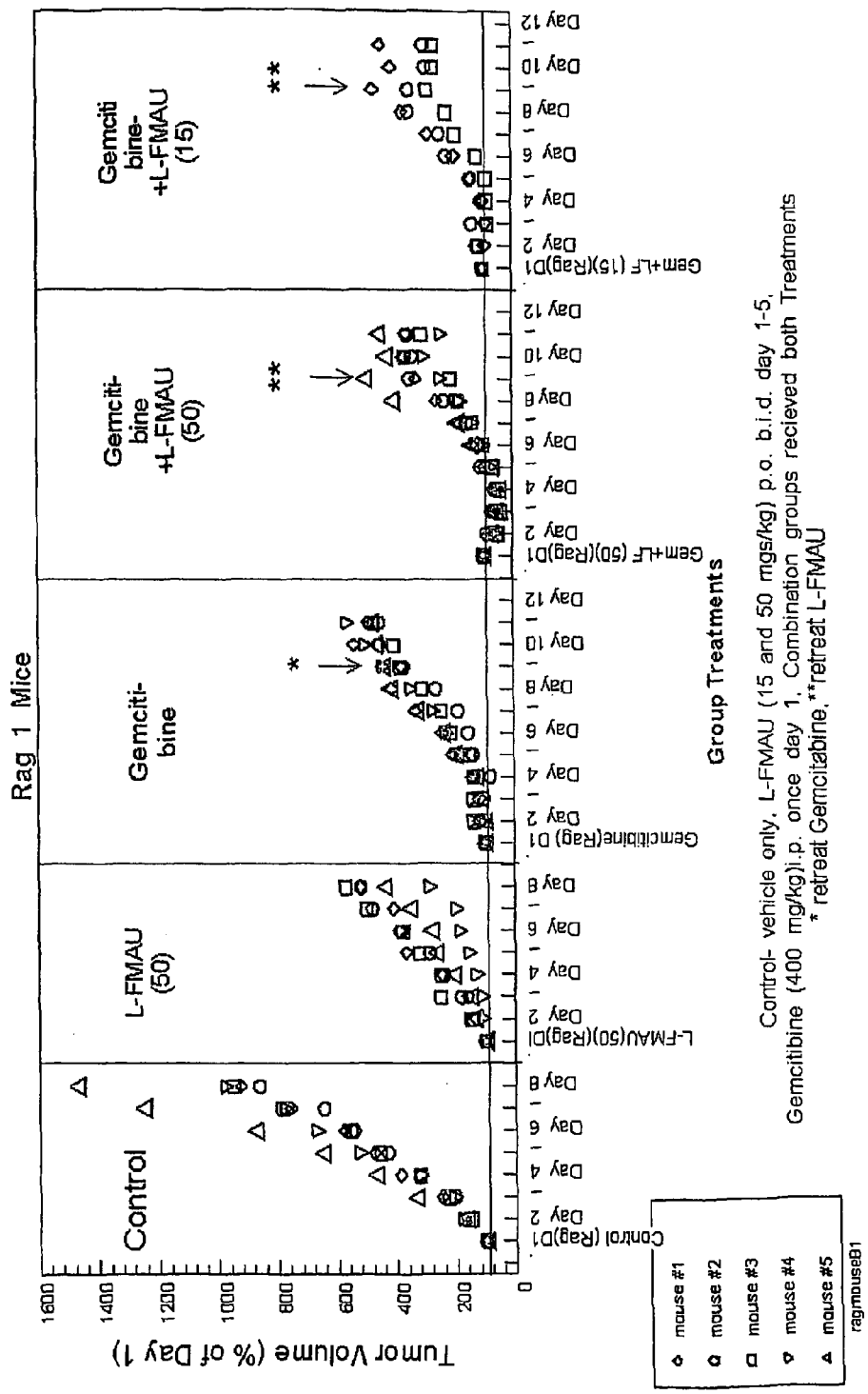
Figure 12:
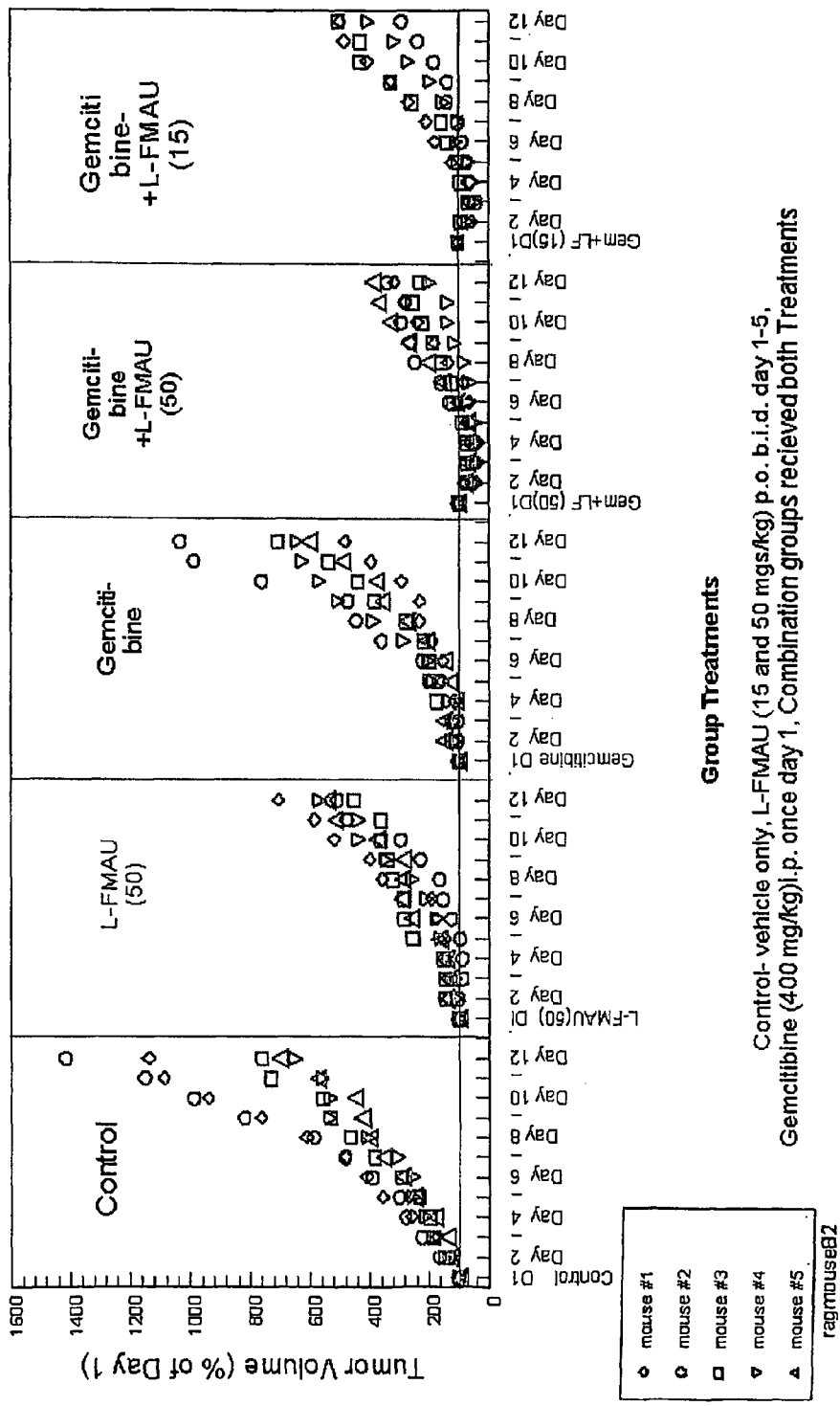

Experiment 10 tested the effects of L-FMAU on the enhancement of anti-cancer drug effect (gemcitabine 400 mg/kg i.p. once on day 1) as indicated in FIGS. 10-12 on Rag 1 mouse (severe combined immunodeficiency—no production of mature T cells or B cells). In this experiment, the murine tumor colon 38 was planted into Rag 1 mice and C57B1 immunodeficient (but with mature T cell production) mice. Gemcitabine was given once on day one (400 mg/kg) ip and LFMAU was given on days 1-5 at two different concentrations (15+50 mg/kg).

The results, which are set forth in attached FIGS. 10-12 evidence that L-FMAU exhibited anti-tumor effect in both groups. L-FMAU worked better with gemcitabine in both groups. L-FMAU at 15 mg/kg with gemcitabine was slightly better in the immunocompetent C57B1 group suggesting T cell involvement as experienced in earlier experiments. Significant major effect of interaction was not effected by lack of T cells and decreased B cells.

The invention claimed is:

1. A method of treating cancer in a patient or subject in need thereof comprising administering to said patient an effective amount of at least one compound according to the structure:

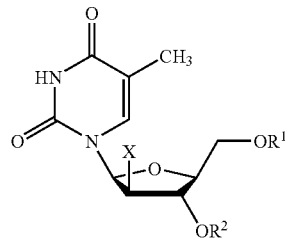

Where X is H or F;
R$^1$ and R$^2$ are independently H, an acyl group, a $C_1$-$C_{20}$ alkyl or ether group, a phosphate, diphosphate, triphosphate or a phospliodiester group, or a pharmaceutically acceptable salt thereof, wherein said cancer is stomach, colon, rectal, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma cancer.

2. The method according to claim 1 wherein said patient or subject is a human and R$^1$ and R$^2$ are each independently H, a $C_2$-$C_{18}$ acyl group or a phosphate group.

3. The method according to claim 2 wherein X is F.

4. The method according to claim 1 wherein said cancer is a cancerous tumor.

5. The method according to claim 2 wherein said cancer is selected from the group consisting of colon, rectal, pancreatic and melanoma.

6. The method according to claim 2 wherein said cancer is pancreatic cancer or leukemia.

7. The method according to claim 2 wherein said cancer is pancreatic or colon.

8. The method according to claim 2 wherein said cancer is bladder or pancreatic.

9. The method according to claim 2 wherein said cancer is prostate or pancreatic.

10. The method according to claim 2 wherein said cancer is breast or pancreatic.

11. The method according to claim 2 wherein said cancer is lung or pancreatic.

12. The method according to claim 2 wherein said cancer is nasopharyngeal or pancreatic.

13. The method according to claim 2 wherein said cancer is ovarian or pancreatic.

14. The method according to claim 2 wherein said cancer is lymphoma or pancreatic.

15. The method according to claim 2 wherein said cancer is melanoma or pancreatic.

16. A method of treating cancer in a patient or subject in need thereof comprising administering to said patient an effective amount of at least one compound according to the structure:

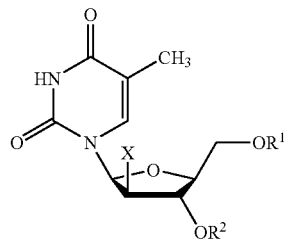

Where X is H or F;

$R^1$ and $R^2$ are independently H, an acyl group, a $C_1$-$C_{20}$ alkyl or ether group, a phosphate, diphosphate, triphosphate or a phosphodiester group, and pharmaceutically acceptable salts thereof in combination with at least one additional anticancer agent, wherein said cancer is stomach, colon, rectal, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma cancer.

17. The method according to claim 16 wherein said patient or subject is a human and $R^1$ and $R^2$ are each independently H or a $C_2$-$C_{18}$ acyl group.

18. The method according to claim 16 wherein said patient or subject is a human and $R^1$ and $R^2$ are each H.

19. The method according to claim 16 wherein said additional anticancer agent is an antimetabolite, an inhibitor of topoisomerase I and II, an alkylating agent or a microtubule inhibitor.

20. The method according to claim 17 wherein said additional anticancer agent is an antimetabolite, an inhibitor of topoisomerase I and II, an alkylating agent or a microtubule inhibitor.

21. The method according to claim 18 wherein said additional anticancer agent is an antimetabolite, an inhibitor of topoisomerase I and II, an alkylating agent or a microtubule inhibitor.

22. The method according to claim 16 wherein said additional anti-cancer compound is selected from the group consisting of Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Deuileukin diftitox, dexrazoxane; docetaxel; doxorubicin; doxorubicin liposomal; Dromostanolone propionate; Elliott's B Solution; epirubicin; Epoctin alfa estramustine; etoposide phosphate; etoposide (VP-16); exemestane; Filgrastim; floxuridine (intraarterial); fludarabine; fluorouracil (5-FU); fulvestrant; gemeitabine, gemtuzumab ozogamicin; gleevec; goserelin acetate; hydroxyurea; Ibritumomah Tiuxetan; idarubicin; ifosfamide; imatimib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mereaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof.

23. The method according to claim 17 wherein said additional anti-cancer compound is selected from the group consisting of Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemcitabine, gemtuzumab ozogamicin; gleevec; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifeu; tarceva; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof.

24. The method according to claim 18 wherein said additional anti-cancer compound is selected from the group consisting of Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin, liposomal; daunorubicin, daunomycin; Denilcukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemcitabine, gemtuzumab ozogamicin; gleevec; goserelin acetate; hydroxyurea; Ibritumomab Tiuxetan; idarubicin; ifosfamide; imatinib mesylate; interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof.

25. The method according to claim 16 wherein X is F.
26. The method according to claim 17 wherein X is F.
27. The method according to claim 18 wherein X is F.
28. The method according to claim 19 wherein X is F.
29. The method according to claim 17 wherein said cancer is a cancerous tumor.
30. The method according to claim 17 wherein said cancer is selected from the group consisting of colon, rectal, pancreatic and melanoma.
31. The method according to claim 17 wherein said cancer is pancreatic cancer or leukemia.
32. The method according to claim 17 wherein said cancer is pancreatic or colon.
33. The method according, to claim 17 wherein said cancer is bladder or pancreatic.
34. The method according to claim 17 wherein said cancer is prostate or pancreatic.
35. The method according to claim 17 wherein said cancer is breast or pancreatic.
36. The method according to claim 17 wherein said cancer is lung or pancreatic.
37. The method according to claim 17 wherein said cancer is nasopharyngeal or pancreatic.
38. The method according to claim 17 wherein said cancer is ovarian or pancreatic.
39. The method according to claim 17 wherein said cancer is lymphoma or pancreatic.
40. The method according to claim 17 wherein said cancer is melanoma or pancreatic.
41. The method according to claim 17 wherein said cancer is pancreatic.
42. The method according to claim 17 wherein said additional anticancer agent is fluorouracil, oxaliplatin, gemeitabine or mixtures thereof.

* * * * *